United States Patent [19]
Cassatt et al.

[11] 4,164,874
[45] Aug. 21, 1979

[54] FLAW GROWTH CORRELATOR

[75] Inventors: Gary G. Cassatt; Richard J. Miller, both of Wichita, Kans.

[73] Assignee: Boeing Wichita Company, Wichita, Kans.

[21] Appl. No.: 870,616

[22] Filed: Jan. 19, 1978

[51] Int. Cl.² .............................................. G01N 3/32
[52] U.S. Cl. ..................................................... 73/799
[58] Field of Search ................... 73/88 R, 91, 95, 799

[56] References Cited
U.S. PATENT DOCUMENTS

| 2,920,480 | 1/1960 | Haas | 73/88 R |
| 3,136,154 | 6/1964 | Christensen | 73/88 R |

*Primary Examiner*—Jerry W. Myracle
*Attorney, Agent, or Firm*—Edwin H. Crabtree

[57] ABSTRACT

A flaw growth correlator for monitoring flaw growth potential in a structural body. The correlator providing a major increase in the sensitivity of flaw growth when compared to current designs of constant thickness crack gauges.

15 Claims, 13 Drawing Figures

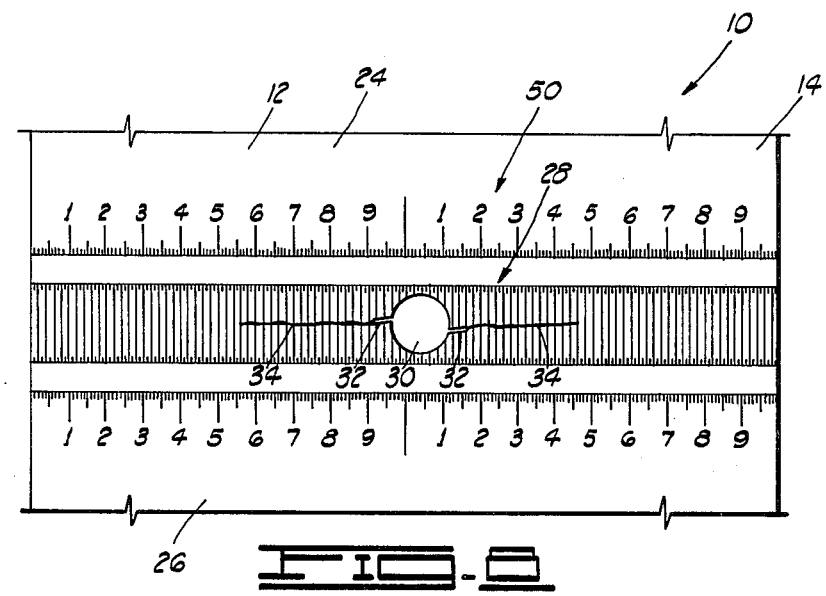
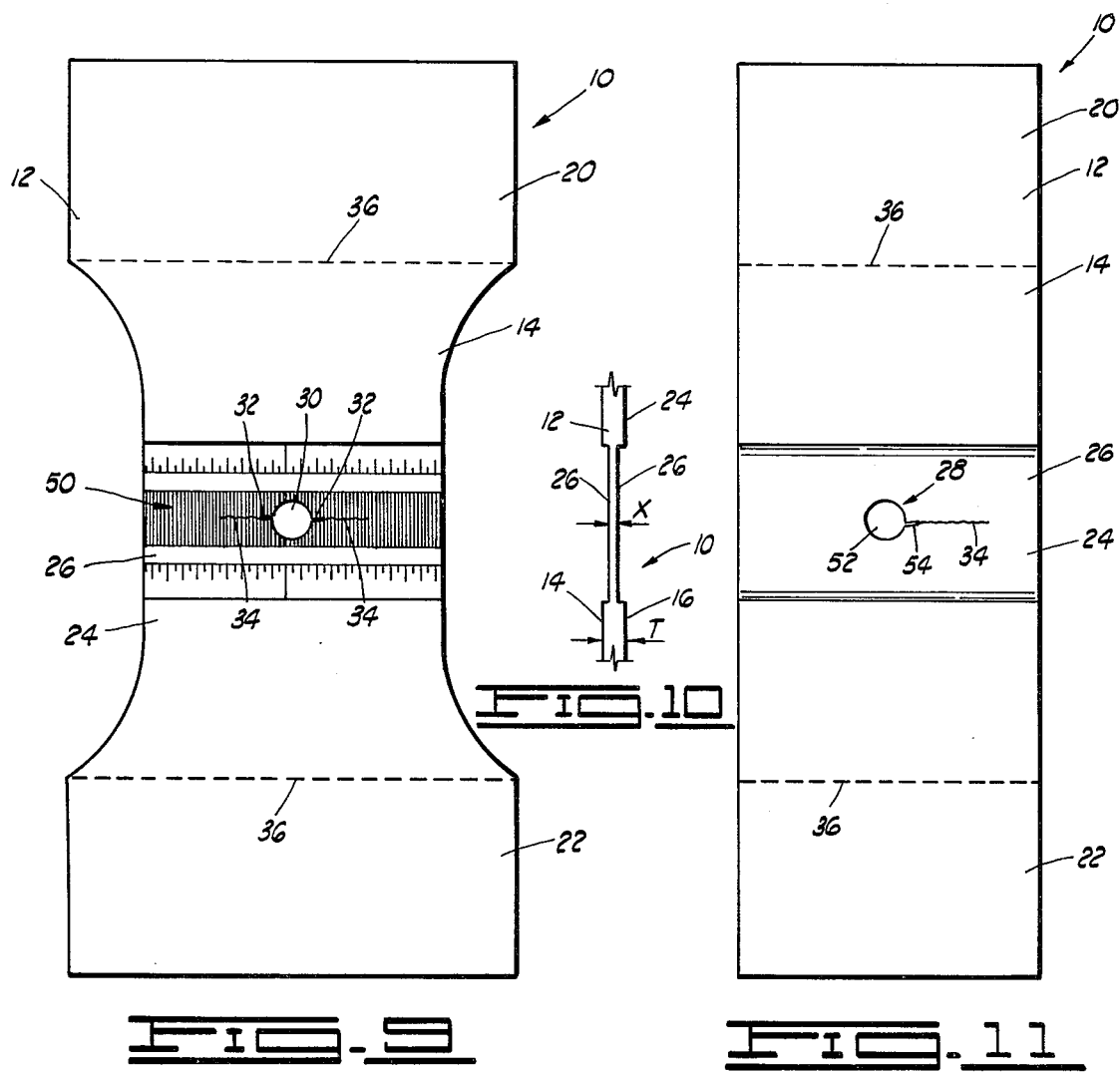

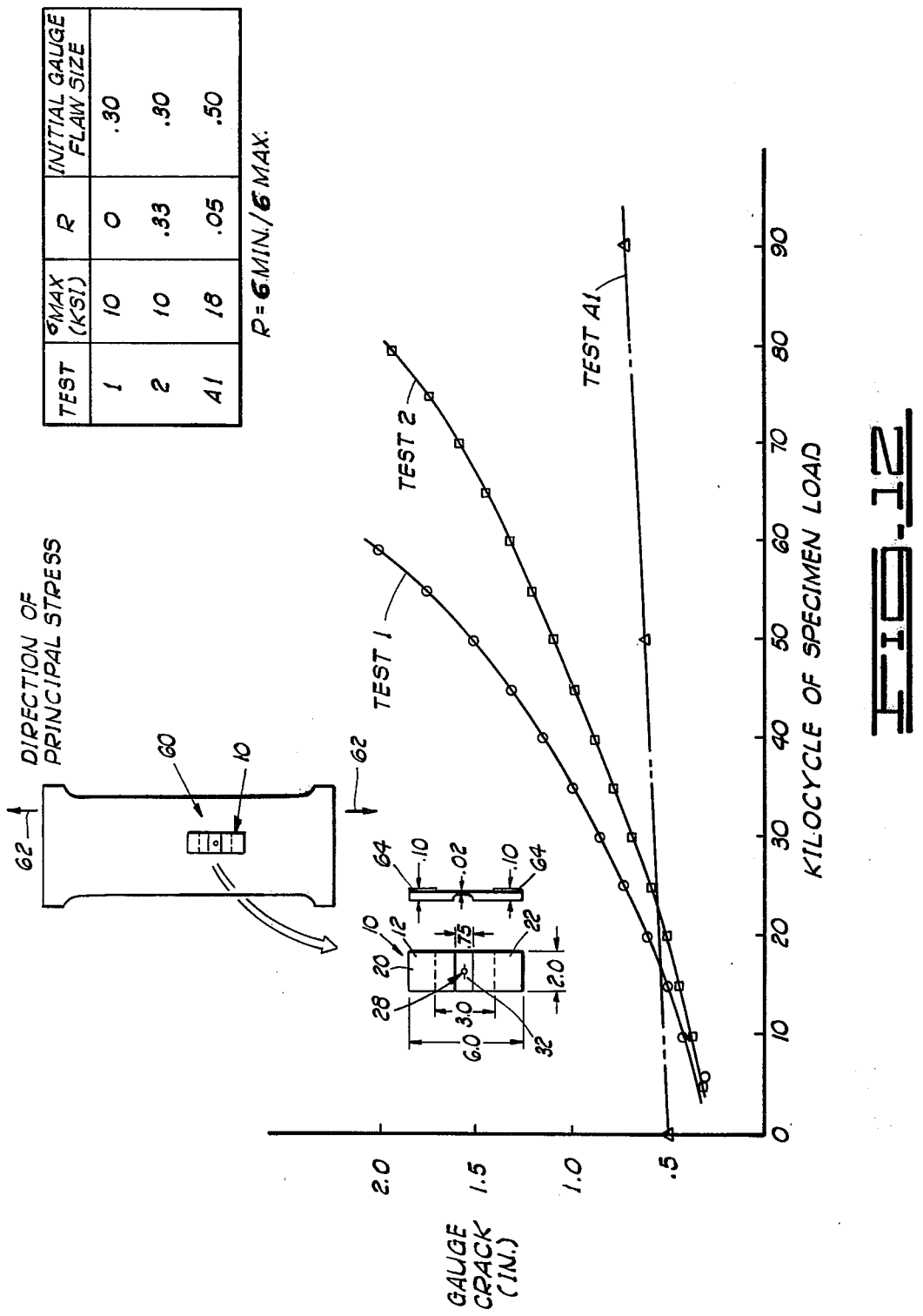

FLAW GROWTH CORRELATOR

BACKGROUND OF THE INVENTION

This invention relates to flaw growth monitors or indicators and in particular, but not by way of limitation, to an improved flaw growth correlator for monitoring aircraft flaw growth potential in metal structures.

In U.S. Pat. No. 2,920,480 to Haas and U.S. Pat. No. 3,136,154 to Christensen metal stress monitors are disclosed for attaching to a metal surface. The monitors include metal coupons bonded to the metal surface and having notches, holes, strain gauges, or the like for measuring stress across the area of the coupon so that a correlation may be made between the stress failure of the coupon and potential failure of the metal surface under test.

More recently, U.S. Pat. No. 3,979,949 to Smith discloses a fatigue damage indicator for measuring accumulated fatigue damage on a metal surface. The indicator includes a metal base of uniform thickness with a narrow crack-like slit in the side of the base and having a Teflon parting strip underlying the slit. When the indicator is attached to a metal structure subjected to repeated loading, a correlation may be made between the growth of a crack from the slit and potential fatigue damage incurred in the metal structure.

While the above prior art patents disclose various types of indicators for measuring stress damage using a gauge, coupon, etc., attached to the metal surface under test, none of the indicators provide for accelerated flaw growth in the gauge so that potential flaw growth in a metal surface can be quickly detected and failure of the metal surface may be averted.

SUMMARY OF THE INVENTION

The subject flaw growth correlator provides a major increase in the sensitivity of flaw growth over prior fatigue damage indicators and monitors. The invention further provides for the rapid growth of a crack from a crack-initiating stress raiser for correlating with potential growth of imperfections in the metal structure of an aircraft or any similar metal structure under test. Also, the amount of flaw growth may be more accurately determined when compared with the flaw growth of crack gauges having a constant thickness.

The flaw growth correlator for monitoring flaw growth potential in a structural body includes a flat metal gauge having a first end portion and a second end portion with a center portion therebetween. The first end portion and second end portion are used for securing the gauge to the top of the structural body. The center portion includes a necked down area having a thickness less than the overall thickness of the gauge. A crack-initiating stress raiser is disposed in the necked down area of the center portion of the gauge. By introducing the crack-initiating stress raiser in the necked down area of the center portion, the correlator provides a major increase in the sensitivity of the flaw growth originating from the crack-initiating stress raiser. The amount of flaw growth is compared with the flaw growth of cracks in the structural body so that a proper maintainance time period may be determined for correcting the flaws in the structural body prior to excessive fatigue or failure of the body occurs.

The advantages and objects of the invention will become evident from the following detailed description when read in conjunction with the accompanying drawings which illustrate the preferred embodiments of the invention.

BRIEF DESCRIPTION OF THE DRAWINGS

FIG. 8 is an enlarged top sectional view of the correlator showing a measurement scale for quickly measuring the amount of crack growth.

FIG. 9 is a top view of the measurement scale applied to the correlator shown in FIG. 3.

FIG. 10 shows a partial side view of the correlator of FIG. 9.

FIG. 11 illustrates an alternate embodiment of the correlator.

FIG. 12 illustrates test results of the subject invention when compared with a constant thickness crack gauge.

DETAILED DESCRIPTION OF THE DRAWINGS

Figure 1:
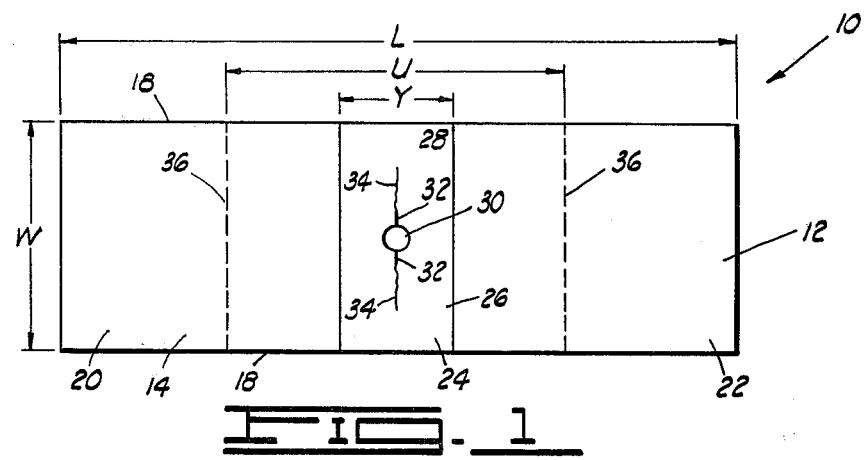
In FIG. 1, a top view of the correlator is illustrated.

In FIG. 1, the flaw growth correlator is designated by general reference numeral 10. The correlator 10 includes a flat angular shaped metal gauge 12 having a top 14, a bottom 16 (shown in FIG. 2), sides 18, and a first end portion 20, a second end portion 22, and a center portion 24. The gauge 12 may be made of aluminum, steel, or any other material. The gauge material should be similar to the material making up the structural body under stress load to which it is attached.

The gauge 12 includes the following dimensions. A length designated by the letter (L), which may vary anywhere from two inches to twelve inches long and is typically in the area of six inches long. A width (W) which varies from one inch to four inches and is typically two inches wide. A thickness (T) shown in FIG. 2, which varies from 0.08 inches to 0.25 inches and is typically in the area of 0.10 inches. It should be appreciated that the above dimensions could be greater or less depending on the type of structural body under test and still be within the scope of the subject invention.

Figure 2:
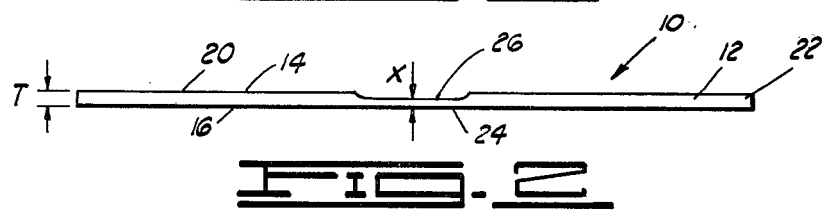
FIG. 2 is a side view of the correlator shown in FIG. 1.

In the center portion 24 of the gauge 12 is a necked down area 26 having a length (Y) and a thickness (X) shown in FIG. 2. The thickness (X) of the necked down area 26 is always less than the thickness (T) and is in a range of 0.01 to 0.10 inches and typically is 0.02 inches thick. The length of the center portion 24 is (U).

Disposed in the necked down area 26 of the center portion 24 is a crack-initiating stress raiser 28. In this Figure, the stress raiser 28 includes cut slits 32 extending outwardly from an aperture 30. The slits 32 are parallel to the width (W) and provide the starting point of crack growth shown as wavy lines 34. The growth of the lines 34 continue outwardly as the gauge 12 is placed under a continuous stress load.

Also shown in FIG. 1 are dotted lines 36 which define an area in the first end portion 20 and second end portion 22 which is used for securing the gauge 12 to the structural body such as a metal surface of an aircraft. It should be noted that while the correlator 10 is principally designed for determining crack growth around fastener holes, imperfections in metal surfaces, and high stress areas in the construction of aircraft, the correlator 10 could be used equally well in testing other types of structural bodies and metal surfaces. The area bounded by the length (U) and the width (W) representing the center portion 24 of the gauge 12 is unsecured or unbonded to the structural body. The length (U) will vary in length depending on how the gauge is secured. Varying the length (U) allows adjustment of sensitivity of crack growth rate in the gauge.

In FIG. 2, a side view of the gauge 12 can be seen with the necked down portion 26 in the center portion 24. It has been found that by providing the necked down area 26 in the center portion 24 of the gauge 12 and across the width (W) that crack-initiating stress raisers such as the aperture 30 with cut slits 32, and other similar type crack-initiating stress raisers, the growth of cracks outwardly from the crack-initiating stress raisers in the gauge 12 are greatly accelerated. This configuration of the gauge 12 appears to have a synergistic effect as to flaw growth when compared to prior art gauges having a uniform thickness.

Figure 3:
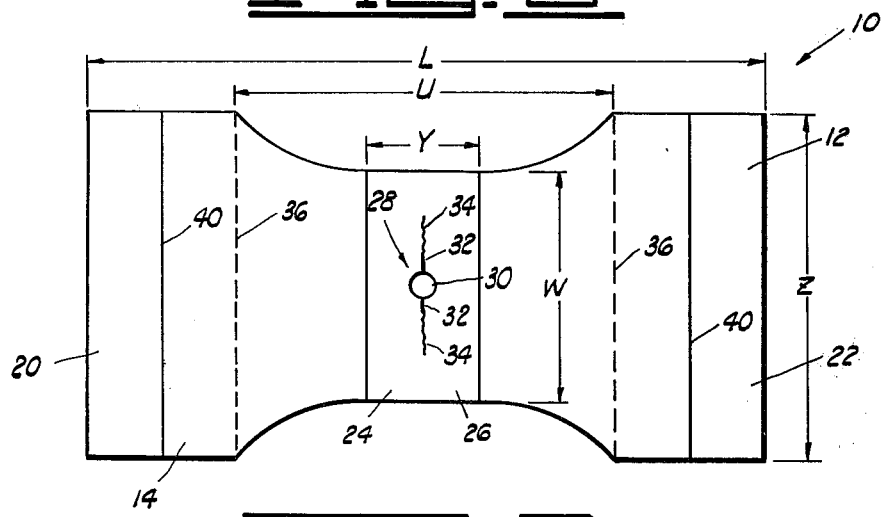
FIG. 3 is an alternate embodiment of the correlator.

In FIG. 3, an alternate embodiment of the correlator 10 is disclosed wherein the first end portion 20 and second end portion 22 are flared outwardly from the overall width (W) of the gauge 12. The increased width, designated by dimension (Z), provides an increased area for securing the gauge 12 to the structural body under test.

Figure 4:
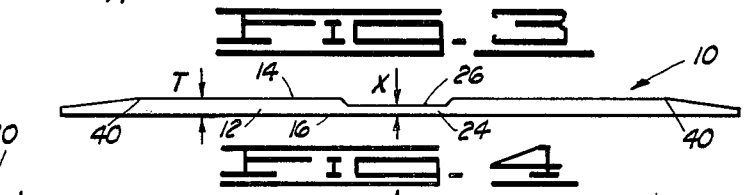
FIG. 4 is a side view of the correlator shown in FIG. 3.

In FIG. 4, a side view of the correlator 10 shown in FIG. 3 is illustrated. To provide a less abrupt discontinuity for the bonding agent underneath the gauge 12 and at the bottom 16 of the first end portion 20 and second end portion 22 is a tapered portion 40. The gauge may be secured to the structural body by adhesive bonding agents or in the alternative rivets, bolts, or any other similar securing means may be used.

Figures 5, 6, 7:
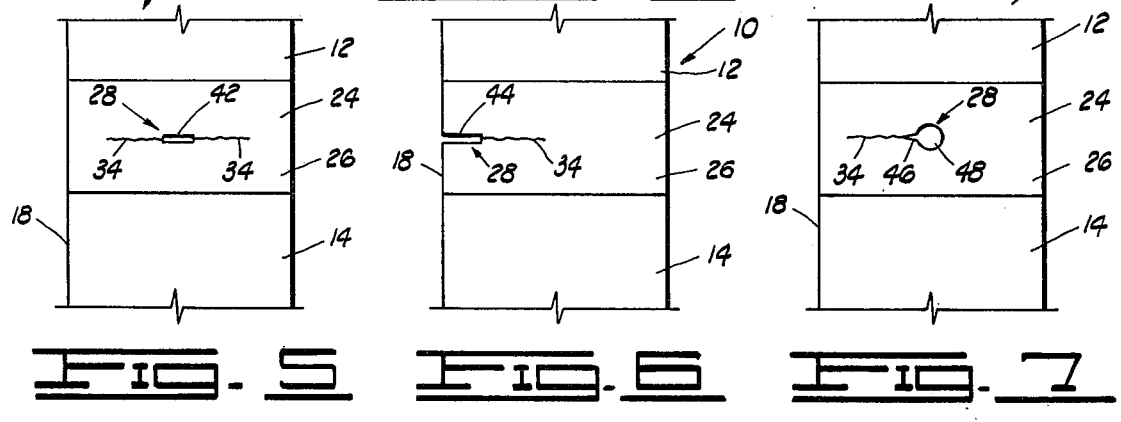
FIGS. 5, 6 and 7 illustrate alternate ways of applying a crack-initiating stress raiser to the correlator.

In FIG. 5, a partial top view of the correlator 10 is illustrated wherein the stress raiser 28 is a cut slit 42 typically 0.005 inches wide produced by electrical discharge machining parallel to the width (W) and in the center of the necked down area 26 of the center portion 24.

In FIG. 6, the stress raiser 28 is illustrated as a cut slit 44 in the side 18 of the gauge 12 and in the necked down area 26 of the center portion 24.

In FIG. 7, the stress raiser 28 is illustrated as a notch 46 in the side of an aperture 48. It should be appreciated that while slits 32, 42, 44, and notch 46 are shown, other geometric figures may be used equally well as stress raisers for introducing flaw growth in the necked down area 26 of the center portion 24 of the gauge 12.

In FIG. 8, a partial top view of the center portion 24 of the gauge 12 is illustrated. In this view, an enlarged scale 50 is illustrated having lined spacing for measuring the length of the crack growth originating from the slits 32 cut in the sides of the aperture 30. The scale 50 is applied in the necked down area 26 on the top 14 of the gauge 12 by photographic etch processing or any other means of applying a scale thereto. It should be noted in this view that the crack growth represented by lines 34 is approximately 0.3 of an inch. When the accelerated crack growth in the gauge 12 is properly correlated with the crack growth in the structural body, the limit of crack growth may be determined. For example, if the crack growth in gauge 12 is over 1 inch under a predetermined load time history, this would indicate an appropriate crack growth of 0.25 inches in the structural body and the metal surface is in a dangerous condition requiring maintenance repair. This correlation is discussed more fully under FIG. 13.

In FIG. 9, the correlator 10 shown in FIG. 3 is illustrated with the scale 50 applied to the area 26 of the center portion 24 of the gauge 12.

In FIG. 10, a side sectional view of the gauge 12, shown in FIG. 9, is illustrated. It should be noted in this Figure, the necked down portion 26 extends inwardly from both the top 14 and bottom 16 of the gauge 12 to produce an overall thickness (X) which again is less than the overall thickness (T) of the gauge 12. The necked down area 26 is symmetrical as to being equal distance from the top 14 and bottom 16 of the gauge 12. The necked down area 26 could be at different distances in depth from the top 14 and bottom 16 of the gauge 12 as long as the overall thickness (X) is less than the thickness (T) of the gauge 12.

FIG. 11 illustrates another alternate embodiment of the stress raiser 28 wherein an aperture 52 is illustrated having a single cut slit 54 and a crack growth represented by the line 34 extending outwardly and parallel to the width (W) of the gauge 12.

In FIG. 12, the test results of the subject invention is illustrated in comparison to the fatigue damage indicator disclosed in U.S. Pat. No. 3,979,949 and represented by a line marked "Test A1".

A graph is shown in this Figure having a horizontal line marked from 0 through 90 and representing kilocycles of specimen load and a vertical line representing the gauge crack growth in inches from 0 to 2.0 inches.

A structural body such as an aircraft wing is represented by a specimen 60 which under test is shown having arrows 62 representing the direction of the principal stress placed on the specimen 60. The typical dimensions of the gauge 12 are shown wherein the overall length is six inches, the width two inches, the length of the necked down area 0.75 inches and having a thickness of 0.02 inches. The unbonded length of the gauge 12 is 3.0 inches. The thickness of the gauge 12 is 0.10. The gauge 12 is also shown with an adhesive bonding agent 64 applied to the bottom of the first end portion 20 and second end portion 22 for securing the gauge 12 to the specimen 60.

In the testing of the fatigue damage indicator in Test A1, the indicator was applied a stress load of from 0 pounds per square inch to 18,000 pounds per square inch with an initial flaw size of 0.50 inches. At 50 kilocycles of specimen load, the crack originating from the initial flaw grew to approximately 0.6 inches, indicating a crack growth of 0.1 inches. At 90 kilocycles, the crack growth grew from 0.5 to approximately 0.7 inches, indicating a crack growth of 0.2 inches.

In both Tests 1 and 2, the subject invention is used except the ratio (R) or the minimum load per square inch to the maximum load per square inch is varied from 0 in Test 1 to 0.33 in Test 2. In Test A1, the ratio (R) was 0.05 or very similar to the ratio (R) of Test 1.

In Test 1, the initial flaw size is 0.3 inches. At 50 kilocycles, a crack growth of approximately 1.5 inches has occurred indicating a growth of approximately 1.2 inches. At 60 kilocycles, the flaw growth has increased to approximately 2.0 inches indicating an overall growth of 1.7 inches.

In Test 2, the accelerated growth of the flaw is not as great as Test 1, but in comparison is greatly accelerated when compared to the fatigue damage indicator used in Test A1. In the case of Test 2, at 50 kilocycles, the flaw growth is approximately 1.1 inches, indicating an overall growth of 0.8 inches. At 80 kilocycles, the flaw growth is a approximately 1.9 inches, indicating an overall growth of 1.6 inches.

As the graph in FIG. 12 clearly illustrates, the subject invention using the necked down area 26 having a thickness (X) which is less than the overall thickness (T) of the gauge 12 greatly accelerates crack growth originating from the stress riser 28. This feature providing crack growth greater than 10 times the crack growth originating from a crack-initiating slit in a metal base of the fatigue damage indicator described in U.S. Pat. No. 3,979,949.

Figure 13:
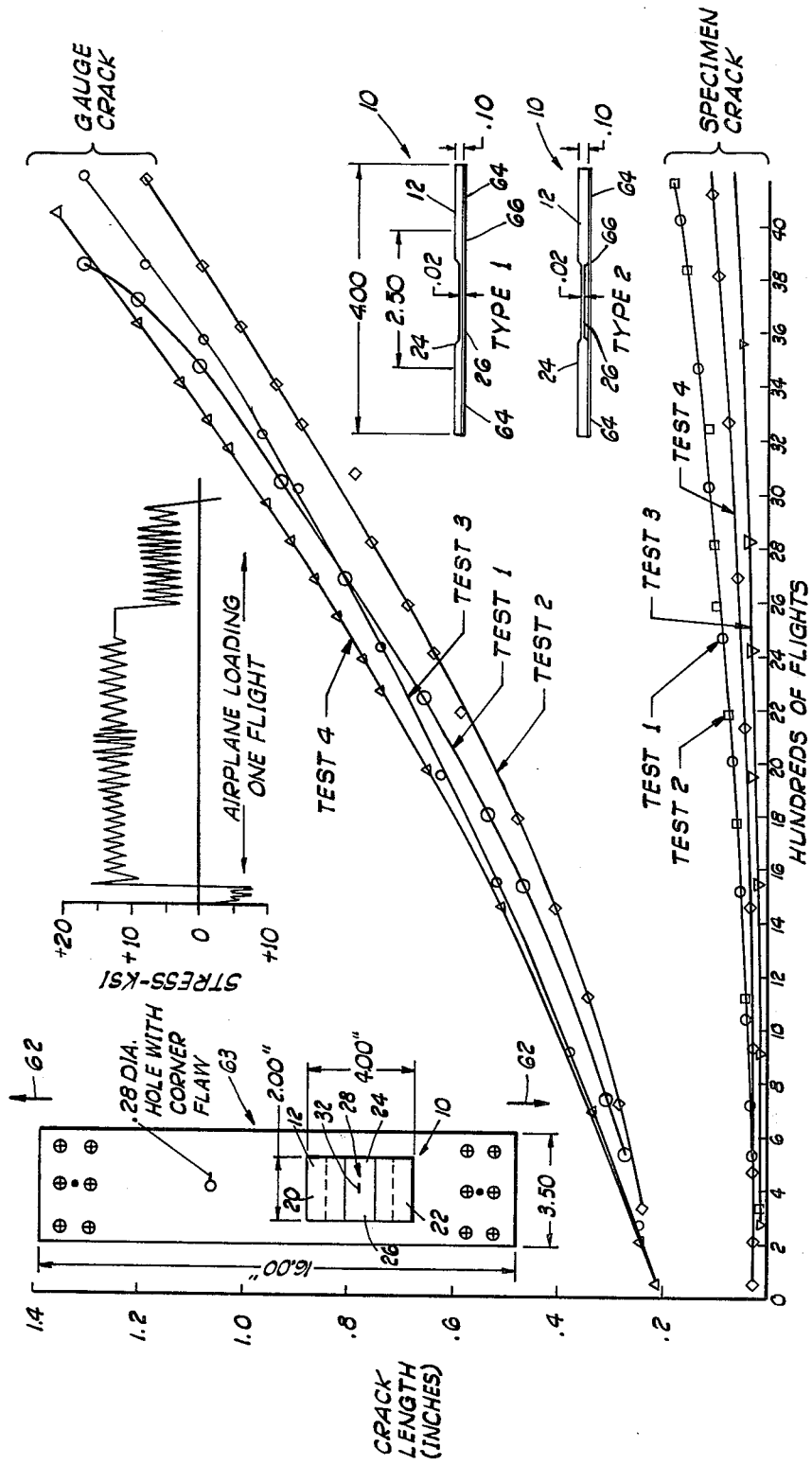
FIG. 13 illustrates test results of the subject invention when compared with crack growth in a test specimen of a structural body.

In FIG. 13 test results of crack growth of the subject invention are illustrated compared to the crack growth in the test specimen 63. These results demonstrate the ability of the correlator 10 to accelerate flaw growth over flaw growth in an aircraft structure or any other metal structure. This correlation provides an intelligent estimate of potential flaw sizes and growth rates at remote locations which are difficult to inspect such as the inside of an aircraft wing or body structure.

In the test, the gauge 12 discussed under FIG. 1 and FIG. 2 having a necked down portion 26 is tested and indicated as Type 1. The gauge 12 shown in FIGS. 9 and 10 having a symmetrical necked down area 26 is tested and indicated as Type 2. The Type 1 gauge 12 was used in Test 1 and Test 2. The Type 2 gauge 12 was used in Test 3 and Test 4. The gauges 12 are used in all four tests have similar dimensions with an overall length of 4 inches, a width of 2 inches, an unbonded length of 2.5 inches, an overall thickness (T) of 0.10 inches and an overall thickness (X) in the necked down portion 26 of 0.02 inches. The crack-initiating slit 32 is 0.20 inches long and having a width of 0.005 inches. The Type 1 and Type 2 gauges 12 were attached to the specimen 63 by an adhesive 64 with a Teflon strip 66 disposed underneath the unbonded area of the gauge 12.

The specimen 63 is 16 inches long with a width of 3.5 inches. The thickness (T) of the specimen 63 is 0.25 inches. The specimen 63 includes a 0.28 inch diameter hole with a corner flaw therein as a stress riser for initiating crack growth in the specimen 63.

The horizontal line of the graph shown in FIG. 13 illustrates hundreds of flights with each flight having an airplane loading initially of approximately −8.0 KSI which is increased upwardly to a high of approximately +17.0 KSI before dropping into a range of 3.0 to 8.0 KSI and dropping downwardly to a −5.0 KSI at the end of the flight. The vertical line of the graph illustrates the crack length in inches of the flaw in the specimen 63 and the crack growth of the slit 32 of the gauge 12.

In viewing the graph at 1,000 flights, the crack growth of the specimen 63 has grown very little, while the crack growth from the slit 32 has grown from 0.2 inches to a range of 0.25 to 0.4 inches, depending on which Test, 1 through 4, is read. At 2,000 flights, the crack growth of the specimen 63 has grown in a range of 0.03 to 0.08 inches. The crack growth of Type 1 and Type 2 gauges 12 have now grown in a range of 0.5 to over 0.6 inches in length. At 3,000 flights, the crack growth of the specimen 63 is in a range of 0.05 to 0.1 inches. The growth of the slit 32 in the gauges 12 are in a range of 0.8 inches to 1 inch. At 4,000 flights, the crack growth of the specimen is from 0.05 to 0.2 inches, while the range of the crack growth in the gauges 12 have a minimum growth of 1.2 inches and a maximum growth of over 1.4 inches.

As can be appreciated from reviewing the plotted curves from Tests 1, 2, 3, and 4 wherein the individual crack growth in the Type 1 and Type 2 gauges 12 are measured against the crack growth initiating from the corner flaw of the hole in the specimen 63, the accelerated crack growth in the correlator 10 is in a range of 10 times as great as the normal crack growth in a metal aircraft structure represented by the specimen 63.

Changes may be made in the construction and arrangement of the parts or elements of the embodiment as disclosed herein without departing from the spirit or scope of the invention as defined in the following claims.

We claim:

1. A flaw growth correlator for monitoring flaw growth potential in a structural body, the correlator comprising:
   a flat metal gauge having a top, a bottom, sides, a first end portion, a second end portion, and a center portion, said gauge having a length (L), a width (W), and a thickness (T), the center portion including a necked down area across the width (W) of said gauge and having a thickness (X) less than (T); and
   a crack initiating stress raiser disposed in the necked down area of the center portion of said gauge; an aperture in the necked down area of the center portion of said gauge, said crack-initiating stress raiser extending outwardly from the side of said aperture.

2. The correlator as described in claim 1 wherein said crack-initiating stress raiser is in the side of the center portion of said gauge.

3. The correlator as described in claim 1 wherein said crack-initiating stress raiser is disposed in the center of the necked down area of the center portion of said gauge.

4. The correlator as described in claim 1 further including a second crack-initiating stress raiser extending outwardly from the side of said aperture.

5. The correlator as described in claim 1 further including means for measuring the length of the crack growth on the top of said gauge and parallel to said stress raiser.

6. The correlator as described in claim 1 further including securing means applied to the bottom of the first and second end portions for securing said gauge to the top of the structural body.

7. The correlator as described in claim 6 wherein said securing means is a bonding agent.

8. The correlator as described in claim 7 wherein the bottom of the first and second end portions of said gauge is tapered for relieving severity of bonding discontinuity.

9. The correlator as described in claim 6 wherein said securing means is a rivet, bolt, or the like.

10. The correlator as described in claim 1 wherein the thickness (X) of the necked down area of the center portion of said gauge is in a range of 0.01 to 0.08 inches.

11. The correlator as described in claim 1 wherein the thickness (T) of said gauge is in a range of 0.08 to 0.25 inches.

12. The correlator as described in claim 1 wherein the necked down area of the center portion of said gauge is in the top of said gauge.

13. The correlator as described in claim 1 wherein the necked down area in the center portion of said gauge is in both the bottom and the top of said gauge.

14. The correlator as described in claim 1 wherein said stress raiser is a cut slit, notch, or the like.

15. A flaw growth correlator for monitoring flaw growth potential in a structural body, the correlator comprising:
   a flat angular shaped metal gauge having a top, a bottom, sides, a first end portion, a second end portion, and a center portion, said gauge having a length (L), a width (W), and a thickness (T), the thickness (T) in a range of 0.08 to 0.25 inches, the center portion of said gauge including a necked down area across the width (W) of said gauge and having a thickness (X) less than (T), the thickness (X) in a range of 0.01 to 0.08 inches;
   a crack-initiating stress raiser disposed in the necked down area of the center portion of said gauge and parallel to the width (W) of said gauge;
   means for measuring the length of the crack growth on the top of said gauge and parallel to said stress raiser; and
   securing means applied to the bottom of the first and second end portions for securing said gauge to the surface of the structural body.

* * * * *